United States Patent [19]

Führer et al.

[11] Patent Number: 4,876,253

[45] Date of Patent: Oct. 24, 1989

[54] TRISUBSTITUTED 1,3,5-TRIAZINE-2,4,6-TRIONES

[75] Inventors: Wolfgand Führer, Cologne; Engelbert Kühle, Bergisch Gladbach; Alfons Adler, Cologne; Gerd Hänssler, Leverkusen, all of Fed. Rep. of Germany

[73] Assignee: Bayer Aktiengesellschaft, Leverkusen, Fed. Rep. of Germany

[21] Appl. No.: 182,554

[22] Filed: Apr. 18, 1988

Related U.S. Application Data

[63] Continuation-in-part of Ser. No. 118,110, Nov. 5, 1987, which is a continuation-in-part of Ser. No. 50,981, May 15, 1987, abandoned.

[30] Foreign Application Priority Data

Jun. 3, 1986 [DE] Fed. Rep. of Germany ....... 3618662

[51] Int. Cl.[4] ................... C07D 251/34; A01N 43/66
[52] U.S. Cl. ..................................... 514/241; 544/221
[58] Field of Search ......................................... 514/241

[56] References Cited

U.S. PATENT DOCUMENTS

| | | | |
|---|---|---|---|
| 3,957,778 | 5/1976 | Kauffman | 260/248 |
| 4,053,538 | 10/1977 | Herweh et al. | 260/860 |
| 4,085,268 | 4/1978 | Kauffman | 544/221 |

FOREIGN PATENT DOCUMENTS

0081142 6/1983 European Pat. Off.
2313721 10/1974 Fed. Rep. of Germany.

OTHER PUBLICATIONS

Comptes Rendus, Serie C. vol. 279, Dec. 2, 1974, pp. 969–972, Paris, Fr; A. Etienne et al.: "Isocyanurates Dimethyles-1.3 et aryles-5".
Comptes Rendus, Serie C., vol. 281, Sep. 1, 1975, pp. 275–278, Paris, Fr; A. Etienne et al.: "Isocyanurates de diallyle-1.3 et d'aryle-5".
Comptes Rendus, Serie C., vol. 283, Nov. 8, 1976, pp. 491–494, Paris, Fr.; A. Eitenne et al.: "Isocyanurates N-phenyles et N-dialkyles mixtes".
Collection Czechoslovak Chem. Commun., vol. 47, 1982, pp. 2219–2226; Z. Bukac et al.: "Kinetics of the Cyclotrimerization and Cocyclotrimerization of Isocyanates Catalyzed with Alkali Metals Alkoxides".
Chemcial Abstracts, vol. 92, No. 23, Jun. 9, 1980, p. 680, Abstract No. 198359q, Columbus, Ohio, U.S.: e. Y. A. Davydov et al,.: "NMR Analysis of Products from Cocyclotrimerization of Phenyl- and Chlorohexyl Isocyanates", & Lakokras, Mater, IKH Primen, 1978, (6), 32–4.

*Primary Examiner*—John M. Ford
*Attorney, Agent, or Firm*—Sprung Horn Kramer & Woods

[57] ABSTRACT

Fungicidally active trisubstituted 1,3,5-triazine-2,4,6-trione of the formula

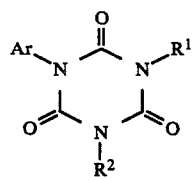

in which
Ar represents optionally substituted aryl,
$R^1$ represents an optionally substituted aliphatic or cycloaliphatic radical and
$R^2$ represents an optionally substituted aliphatic radical,
with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals.

11 Claims, No Drawings

TRISUBSTITUTED 1,3,5-TRIAZINE-2,4,6-TRIONES

This is a continuation-in-part of application Ser. No. 118,110, filed November 5, 1987, now pending, which is a continuation-in-part of application Ser. No. 050,981, filed May 15, 1987, now abandoned.

The invention relates to new trisubstituted 1,3,5-triazine-2,4,6-triones, processes for their preparation and their use for combating pests, in particular as fungicides.

It has already been disclosed that 2-arylamino-4,6-dichloro-s-triazines, such as, for example, 4,6-dichloro-N-(2-chlorophenyl)-1,3,5-triazin-2-amine, have fungicidal properties (compare DAS (German Published Specification) 1,670,675). However, the selective fungicidal activity of these substances is limited to only a few fungi and is not always adequate.

New trisubstituted 1,3,5-triazine-2,4,6-triones of the general formula (I)

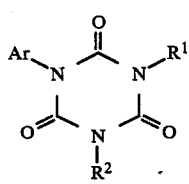

in which
Ar represents optionally substituted aryl,
$R^1$ represents an optionally substituted aliphatic or cycloaliphatic radical and
$R^2$ represents an optionally substituted aliphatic radical, with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals, have been found.

It has furthermore been found that the new trisubstituted 1,3,5-triazine-2,4,6-triones of the formula (I)

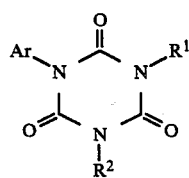

in which
Ar represents optionally substituted aryl,
$R^1$ represents an optionally substituted aliphatic or cycloaliphatic radical and
$R^2$ represents an optionally substituted aliphatic radical, with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals, are obtained either by a process in which
(a) 1-aryl-3-alkyl-1,3,5-triazine-2,4,6-triones of the general formula (II)

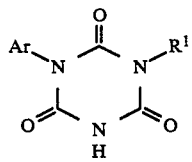

in which Ar and $R^1$ have the abovementioned meanings, are reacted with compounds of the general formula (III)

in which
$R^2$ has the abovementioned meaning and
X denotes a leaving group, such as, for example, halogen or sulphate,
if appropriate in the presence of a diluent and if appropriate in the presence of an acid-binding agent, or by a process in which
(b) in the case where $R^2$ denotes alkyl, N,N'-disubstituted ureas of the general formula (IV)

in which Ar and $R^1$ have the abovementioned meanings,
are reacted with a bischlorocarbonylamine of the general formula

If appropriate in the presence of a diluent and if appropriate in the presence of an acid-binding agent, or by a process in which
(c) in the case where $R^2$ has the meaning given, with the exception of cyanoalkyl, N,N'-dialkylureas of the general formula (VI)

in which
$R^1$ has the abovementioned meaning and
$R^2$ has the meaning given, excluding cyanoalkyl, are reacted with compounds of the general formula (VII)

in which Ar has the abovementioned meaning.

Finally, it has been found that the new trisubstituted 1,3,5-triazine-2,4,6-triones of the formula (I) have very good biological properties and are suitable, above all, for selectively combating harmful fungi in rice.

It is to be described as exceptionally surprising that the substances according to the invention exhibit a better biological activity than known compounds of the prior art of the same type of action and/or sturcturally similar compounds.

Formula (I) provides a general definition of the trisubstituted 1,3,5-triazine-2,4,6-triones according to the invention. Preferred compounds of the formula (I) are those in which Ar represents phenyl, which is optionally mono-, di-, tri-, tetra- or pentasubstituted by identical or different substituents from the group comprising halogen, alkyl with 1 to 4 carbon atoms, halogenoalkyl with 1 to 4 carbon atoms and 1 to 5 identical or different halogen atoms, alkoxy with 1 to 4 carbon atoms, halogenoalkoxy with 1 to 4 carbon atoms and 1 to 5 identical or different halogen atoms, alkythio with 1 to 4 carbon atoms, and halogenoalkylthio with 1 to 4 carbon atoms and 1 to 5 identical or different halogen atoms, or represents halogenosulphonyl, or represents dialkylamino with identical or different straight-chain or branched alkyl radicals with in each case 1 to 4 carbon atoms and/or nitro, $R^1$ represents straight-chain or branched alkyl which has 1 to 12 carbon atoms and is optionally mono-or polysubstituted by identical or different substituents from the group comprising halogen, alkoxy with 1 to 3 carbon atoms, halogenoalkoxy with 1 or 2 carbon atoms and 1 to 5 identical or different halogen atoms, alkylthio with 1 to 3 carbon atoms, halogenoalkylthio with 1 or 2 carbon atoms and 1 to 5 identical or different halogen atoms and furyl and phenyl, which can likewise be mono-, di-, tri-, tetra- or pentasubstituted by identical or different halogen atoms; or represents cycloalkyl which has 3 to 8 carbon atoms and is optionally mono-, di-, tri-, tetra-, penta- or hexasubstituted by identical or different substitutents from the group comprising halogen, alkyl with 1 to 4 carbon atoms, alkoxy with 1 to 3 carbon atoms, halogenoalkoxy with 1 or 2 carbon atoms and 1 to 5 identical or different halogen atoms, alkylthio with 1 to 3 carbon atoms and halogenoalkylthio with 1 or 2 carbon atoms and 1 to 5 identical or different halogen atoms, and $R^2$ represents alkyl with 1 to 4 carbon atoms, alkenyl with 3 to 5 carbon atoms, alkinyl with 3 to 5 carbon atoms, alkoxyalkyl with in each case 1 to 3 carbon atoms in the alkoxy part and in the alkyl part, alkylthioalkyl with in each case 1 to 3 carbon atoms in the alkylthio part and in the alkyl part or alkoxycarbonylalkyl with 1 to 3 carbon atoms in the alkoxy part and 2 or 3 carbon atoms in the alkyl part, or represents cyanoalkyl with 1 to 5 carbon atoms in the alkyl part, with the exclusionary provisos noted hereinabove.

Particularly preferred compounds of the formula (I) are those in which

Ar represents phenyl which is optionally mono-, di-, tri- or tetrasubstituted by identical or different substituents from the group comprising fluorine, chlorine, bromine, alkyl with 1 to 3 carbon atoms, halogenoalkyl with 1 or 2 carbon atoms and 1 to 5 chlorine and/or fluorine atoms, alkoxy with 1 to 3 carbon atoms, halogenoalkoxy with 1 or 2 carbon atoms and 1 to 5 chlorine and/or fluorine atoms, alkylthio with 1 or 2 carbon atoms, halogenoalkylthio with 1 or 2 carbon atoms and 1 to 5 chlorine and/or fluorine atoms, fluorosulphonyl, dialkylamino with identical or different straight-chain or branched alkyl radicals with in each case 1 to 3 carbon atoms and/or nitro, $R^1$ represents straight-chain or branched alkyl which has 1 to 12 carbon atoms and can be mono-, di-, or trisubstituted by identical or different substituents from the group comprising fluorine, chlorine, alkoxy with 1 or 2 carbon atoms, halogenoalkoxy with 1 or 2 carbon atoms and 1 to 3 chlorine and/or fluorine atoms, alkylthio with 1 or 2 carbon atoms, halogenoalkylthio with 1 or 2 carbon atoms and 1 to 3 chlorine and/or fluorine atoms and furyl and phenyl, which can optionally be mono-, di- or trisubstituted by identical or different substituents from the group comprising chlorine and fluorine, or represents cycloalkyl which has 3 to 6 carbon atoms and is optionally mono-, di-, tri-, tetra-, penta- or hexasubstituted by identical or different substituents from the group comprising fluorine, chlorine, alkyl with 1 or 2 carbon atoms, alkoxy with 1 or 2 carbon atoms, halogenoalkoxy with 1 or 2 carbon atoms and 1 to 5 chlorine and/or fluorine atoms, alkylthio with 1 or 2 carbon atoms and halogenoalkylthio with 1 or 2 carbon atoms and with 1 to 3 chlorine and/or fluorine atoms, and $R^2$ represents alkyl with 1 to 3 carbon atoms, alkenyl with 3 or 4 carbon atoms, alkinyl with 3 or 4 carbon atoms, alkoxyalkyl with 1 or 2 carbon atoms in the alkoxy part and 1 to 3 carbon atoms in the alkyl part, alkylthioalkyl with 1 or 2 carbon atoms in the alkylthio part and 1 to 3 carbon atoms in the alkyl part, alkoxycarbonylalkyl with 1 or 2 carbon atoms in the alkoxy part and 2 or 3 carbon atoms in the alkyl part or cyanoalkyl with 1 to 3 carbon atoms in the alkyl part, with the exclusionary provisos noted hereinabove.

Especially preferred compounds of the formula (I) are those in which

Ar represents phenyl which is optionally mono-, di-, tri- or tetrasubstituted by identical or different substituents from the group comprising fluorine, chlorine, methyl, ethyl, isopropyl, trichloromethyl, trifluoromethyl, tetrachloroethyl, tetrafluoroethyl, methoxy, ethoxy, propoxy, trifluoromethoxy, difluorochloromethoxy, trifluoromethylthio, fluorosulphonyl, dimethylamino, diethylamino and nitro, $R^1$ represents straight-chain or branched alkyl with 1 to 12 carbon atoms, in particular isopropyl, sec.-butyl, tert.-butyl, sec.-pentyl, neopentyl, cyclohexyl, furylmethyl or benzyl and $R^2$ represents straight-chain or branched alkyl with 1 to 3 carbon atoms, in particular methyl or ethyl, or represents cyanomethyl, 2-cyanoethyl, methoxycarbonylmethyl, ethoxycarbonylmethyl, n-propoxycarbonylmethyl, allyl or propargyl, with the exclusionary provisos noted hereinabove.

If 1-(3-trifluoromethoxyphenyl)-3-(2,2-dimethylpropyl)-1,3,5-triazine-2,4,6-trione and ethyl iodide are used as starting substances according to process (a), the course of the reaction can be illustrated by the following equation.

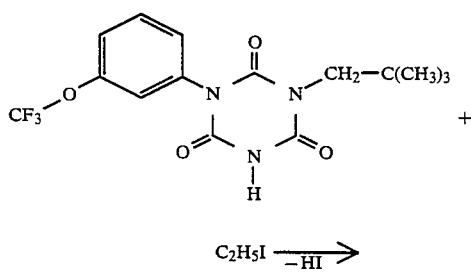

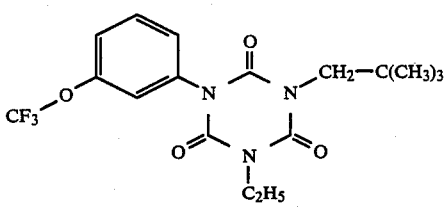

If N-(3,5-dichlorophenyl)-N'-allylurea and bis-chlorocarbonyl-N-methylamine are used as starting substances according to process (b), the course of the reaction can be illustrated by the following equation:

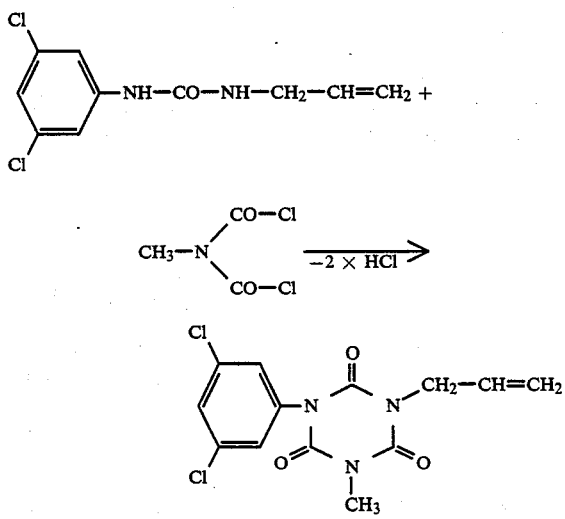

If bis-chlorocarbonyl-N-(2,4-dichlorophenyl)-amine and N-methyl-N'-(2,2-dimethylpropyl)-urea are used as starting substances according to process (c), the course of the reaction can be illustrated by the following equation:

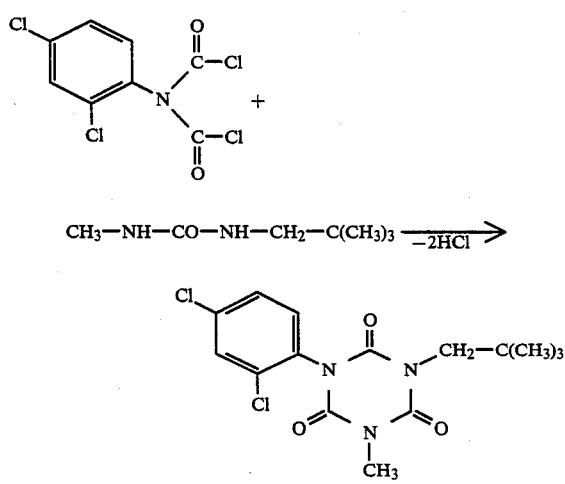

Formula (II) provides a general definition of the di-substituted 1,3,5-triazine-2,4,6-triones required as starting substances in process (a) according to the invention. In this formula, Ar and $R^1$ preferably have the meaning which have already been mentioned in connection with the description of the substances of the formula (I) according to the invention.

The 1,3,5-triazine-2,4,6-triones of the general formula (II) are known in some cases or can be obtained in a manner which is known per se, for example from N,N'-disubstituted ureas (IV) and chlorocarbonylisocyanate (compare Angew. Chem. 89 (1977), 789). The alkylating agents of the formula (III) to be used for process (a) are likewise known. Preferably, in this case, X represents chloride, bromide, iodide or sulphate.

The ureas of the general formulae (IV) and (VI) to be used for processes (b) or (c) according to the invention are known per se and are producible by addition of isocyanates onto primary amines (compare Houben-Weyl: Methoden der organischen Chemie, [Methods of organic chemistry], volume E 4 (1983) page 352, Thieme-Verlag, Stuttgart).

The bis-chlorocarbonylamines of the general formulae (V) and (VII) to be used in process (b) or (c) are likewise known (compare Houben-Weyl: Methoden der organischen Chemie, [Methods of organic chemistry], volume E 4 (1983), page 1022, Thieme-Verlag, Stuttgart).

The reaction temperatures can be varied within a substantial range in the processes according to the invention. The reaction is carried out in general between 20° C. and 150° C., preferably between 50° C. and 120° C., in process (a) and in general between 0° C. and 150° C., preferably between 20° C. and 120° C., in processes (b) and (c).

In carrying out the processes according to the invention, the starting substances and if appropriate the acid-binding agents are employed in approximately equimolar amounts. An excess of acid-binding agents in general does no harm.

The reactions are preferably carried out in the presence of a diluent. Possible diluents are all the inert organic solvents. These include, preferably, hydrocarbons, such as toluene and xylene; chlorinated hydrocarbons, such as chlorobenzene and chloroform; ketones, such as acetone, ethers, such as tetrahdrofurane and dioxane; and nitriles, such as acetonitrile.

All the customary acid-binding agents can be used as the acid-binding agents. These include, preferably, tertiary amines, such as triethylamine and pyridine; alkali metal hydroxides, such as sodium hydroxide and potassium hydroxide, and alkali metal carbonates and bicarbonates, such as potassium carbonate and sodium bicarbonate.

The compounds according to the invention are worked up and isolated in the customary manner. They are in general obtained immediately as crystals or remain as crystals after evaporation of the solvent.

The active compounds according to the invention exhibit a powerful biological action and can be employed in practice for combating undesirable pests. The active compounds are suitable for use, for example, as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;* Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, Pyrisasakii;

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulation in general contain between 0.1 and 95 percent by weight of active compound, preferably between 0.5 and 90%.

The active compounds according to the invention can be present in the formulations as a mixture with other known active compounds, such as fungicides, insecticides and acaricides, and in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

The preparation of the active compounds according to the invention by process (a) can be seen from the following example.

Example

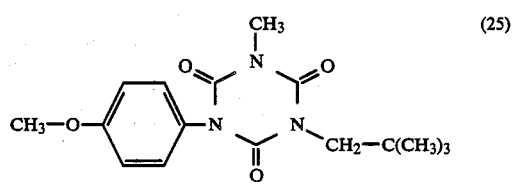

(25)

5.2 g (0.037 mol) of methyliodide are added dropwise to a solution of 10.0 g (0.033 mol) of 1-(4-methoxyphenyl)-3-(2,2-dimethylpropyl)-1,3,5-triazine-2,4,6-trione in 100 ml of absolute acetonitrile and 9 g (0.066 mol) of potassium carbonate at room temperature. The reaction mixture is boiled under reflux for 5 hours. After cooling the solid constituents are separated off and the mother liquor is concentrated under reduced pressure. The residue obtained after stripping off the solvent is ground with cold water for purification. The resulting crystals are filtered off with suction and dried. 10.0 g (95% of theory) of 1-(4-methoxyphenyl)-3-(2,2-dimethylpropyl)-5-methyl-1,3,5-triazine-2,4,6-trione are obtained in this manner in the form of crystals of melting point 134° C., IR:1685 cm$^{-1}$. The substances listed by way of their formulae in the following Table 1 are also prepared by the method just described:

TABLE 1

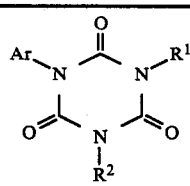

(I)

| Example No. | Ar | R$^1$ | R$^2$ | Physical constants |
|---|---|---|---|---|
| 1 | ―⟨phenyl⟩―O―CF$_2$Cl | ―C$_4$H$_9$―t | ―C$_2$H$_5$ | mp.: 82° C. |
| 2 | ―⟨phenyl⟩―O―CF$_2$Cl | ―CH$_2$―C(CH$_3$)$_3$ | ―CH$_3$ | bp: 196–200° C./ 0.03 mbar |
| 3 | ―⟨phenyl⟩―O―CF$_2$Cl | ―CH$_2$―C(CH$_3$)$_3$ | ―C$_2$H$_5$ | mp.: 92° C. |
| 4 | ―⟨phenyl⟩―N(CH$_3$)$_2$ | ―C$_4$H$_9$―t | ―CH$_3$ | mp.: 130° C. |
| 5 | ―⟨phenyl⟩―N(CH$_3$)$_2$ | ―C$_4$H$_9$―t | ―C$_2$H$_5$ | mp.: 158° C. |
| 6 | ―⟨phenyl⟩―O―CF$_3$ | ―CH$_2$―C(CH$_3$)$_3$ | ―CH$_3$ | mp.: 91° C. |
| 7 | ―⟨phenyl⟩―O―CF$_3$ | ―CH$_2$―C(CH$_3$)$_3$ | ―C$_2$H$_5$ | mp.: 96° C. |

TABLE 1-continued $$\text{(I)}$$

Structure (I): A 1,3,5-triazine-2,4,6-trione ring with Ar on N1, R¹ on N3, R² on N5.

| Example No. | Ar | R¹ | R² | Physical constants |
|---|---|---|---|---|
| 8 | 4-(OCF₃)-C₆H₄– | –CH₂–C(CH₃)₃ | –C₃H₇–n | mp.: 116° C. |
| 9 | 4-(OCF₃)-C₆H₄– | –C₄H₉–t | –CH₃ | mp.: 79° C. |
| 10 | 4-(OCF₃)-C₆H₄– | –C₄H₉–t | –C₂H₅ | mp.: 70° C. |
| 11 | 4-(OCF₃)-C₆H₄– | –C₄H₉–t | –C₃H₇–n | mp.: 90° C. |
| 12 | 4-(OCF₃)-C₆H₄– | –C₄H₉–t | –C₃H₇–iso | $n_D^{20}$: 1.495 |
| 13 | 4-(OCF₃)-C₆H₄– | –C₄H₉–t | –CH₂–CN | mp.: 126° C. |
| 14 | 4-(OCF₃)-C₆H₄– | –C₄H₉–t | –CH₂–CO–O–C₂H₅ | mp.: 82° C. |
| 15 | 4-(OCF₃)-C₆H₄– | –C₃H₇–iso | –CH₃ | mp.: 75° C. |
| 16 | 4-(OCF₃)-C₆H₄– | –C₃H₇–iso | –C₂H₅ | mp.: 83° C. |
| 17 | 4-(OCF₃)-C₆H₄– | –C₃H₇–iso | –C₃H₇–iso | $n_D^{20}$: 1.492 |
| 18 | 4-(OCF₃)-C₆H₄– | –C₃H₇–iso | –CH₂–CN | mp.: 165° C. |

TABLE 1-continued $$\underset{R^2}{\text{Ar}}\underset{N}{\overset{O}{\underset{\|}{\text{N}}}}\underset{O}{\overset{O}{\underset{\|}{\text{N}}}}R^1 \quad (I)$$

| Example No. | Ar | R¹ | R² | Physical constants |
|---|---|---|---|---|
| 19 | 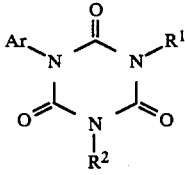 —⟨C₆H₄⟩—O—CF₃ | —C₃H₇—iso | —CH₂—CO—O—C₂H₅ | $n_D^{20}$: 1.486 |
| 20 | 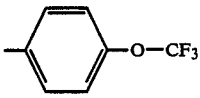 —⟨C₆H₄⟩—O—CF₃ | —CH₃ | —CH₂—CH=CH₂ | Oil; IR: 1695 cm⁻¹ |
| 21 | 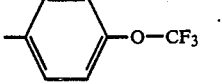 —⟨C₆H₄⟩—O—CF₃ | —CH₂—CN | —CH₃ | mp.: 126° C. |
| 22 | 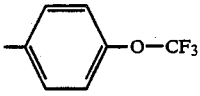 —⟨C₆H₄⟩—O—CF₃ | —C₂H₅ | —CH₃ | mp.: 115° C. |
| 23 | 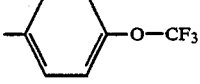 —⟨C₆H₄⟩—O—CF₃ | —CH₃ | —CH(CH₃)—CO—O—CH₃ | Oil; IR: 1695 cm⁻¹ |
| 24 | 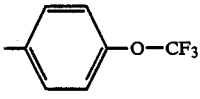 —⟨C₆H₄⟩—O—CF₃ | —CH₃ | —CH₂—CO—O—C₂H₅ | $n_D^{20}$: 1.486 |
| 25 | 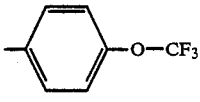 —⟨C₆H₄⟩—O—CH₃ | —CH₂—C(CH₃)₃ | —CH₃ | IR: 1685 cm⁻¹ mp.: 134° C. |
| 26 | 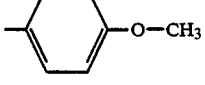 —⟨C₆H₄⟩—O—CH₃ | —CH₂—C(CH₃)₃ | —C₂H₅ | IR: 1680 cm⁻¹ |
| 27 | 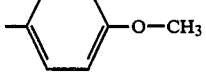 —⟨C₆H₄⟩—O—CH₃ | —CH₂—C(CH₃)₃ | —C₃H₇—n | mp.: 86° C. |
| 28 | 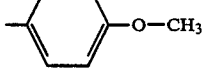 —⟨C₆H₄⟩—O—C₂H₅ | —C₄H₉—t | —CH₃ | mp.: 130° C. |
| 29 | 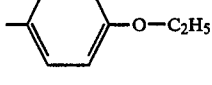 —⟨C₆H₄⟩—O—C₂H₅ | —C₄H₉—t | —C₂H₅ | mp.: 96° C. |
| 30 | 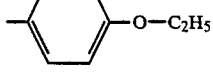 —⟨C₆H₄⟩—O—C₂H₅ | —C₄H₉—t | —C₃H₇—n | mp.: 94° C. |

TABLE 1-continued $$\underset{Ar}{\phantom{XX}}\underset{|}{N}\underset{\phantom{X}}{\overset{O}{\overset{\|}{\diagdown}}}\underset{|}{N}\underset{\phantom{X}}{R^1}$$
(I)

| Example No. | Ar | R¹ | R² | Physical constants |
|---|---|---|---|---|
| 31 | 4-(O—C₂H₅)-C₆H₄— | —CH₂—C(CH₃)₃ | —CH₃ | mp.: 134° C. |
| 32 | 4-(O—C₂H₅)-C₆H₄— | —CH₂—C(CH₃)₃ | —C₂H₅ | mp.: 118° C. |
| 33 | 4-(O—C₂H₅)-C₆H₄— | —CH₂—C(CH₃)₃ | —C₃H₇—iso | IR: 1690 cm⁻¹ |
| 34 | 3-(OCF₃)-C₆H₄— | —CH₂—C(CH₃)₃ | —CH₃ | mp.: 111° C. |
| 35 | 3-(OCF₃)-C₆H₄— | —CH₂—C(CH₃)₃ | —C₂H₅ | bp.: 170° C./ 0.04 mbar |
| 36 | 2-(OCF₃)-C₆H₄— | —C₃H₇—iso | —CH₃ | IR: 1690 cm⁻¹ |
| 37 | 2-(OCF₃)-C₆H₄— | —CH₃ | —CH₂—CH=CH₂ | mp.: 78° C. |
| 38 | 2-(OCF₃)-C₆H₄— | —CH₃ | —CH₂—CN | mp.: 175° C. |
| 39 | 2-(OCF₃)-C₆H₄— | —CH₃ | —CH₂—CO₂C₂H₅ | $n_D^{20}$: 1.482 |
| 40 | 2-(OCF₃)-C₆H₄— | —C₂H₅ | —CH₃ | mp.: 83° C. |

TABLE 1-continued $$\underset{R^2}{\overset{Ar}{\underset{|}{N}}}\text{(triazine-2,4,6-trione with Ar, R}^1\text{, R}^2\text{)} \quad (I)$$

| Example No. | Ar | R¹ | R² | Physical constants |
|---|---|---|---|---|
| 41 | 4-(SCF₃)-C₆H₄– | –C₄H₉–t | –CH₃ | IR: 1680 cm⁻¹ |
| 42 | 4-(SCF₃)-C₆H₄– | –C₄H₉–t | –C₂H₅ | IR: 1695 cm⁻¹ |
| 43 | 4-(SCF₃)-C₆H₄– | –CH₂–C(CH₃)₃ | –CH₃ | mp.: 110° C. |
| 44 | 4-(SCF₃)-C₆H₄– | –CH₂–C(CH₃)₃ | –C₂H₅ | mp.: 92° C. |
| 45 | 4-(SCF₃)-C₆H₄– | –CH₂–C(CH₃)₃ | –C₃H₇–n | mp.: 108° C. |
| 46 | 2-Cl-4-(SCF₃)-C₆H₃– | –C₄H₉–t | –CH₃ | mp.: 96° C. |
| 47 | 2-Cl-4-(SCF₃)-C₆H₃– | –CH₂–C(CH₃)₃ | –CH₃ | Oil; IR: 1695 cm⁻¹ |
| 48 | 2-Cl-4-(SCF₃)-C₆H₃– | –CH₂–C(CH₃)₃ | –C₂H₅ | Oil; IR: 1700 cm⁻¹ |
| 49 | 2-Cl-4-(SCF₃)-C₆H₃– | –CH₂–C(CH₃)₃ | –C₃H₇–n | Oil; IR: 1698 cm⁻¹ |
| 50 | 2,3,5-Cl₃-4-(SCF₃)-C₆H– | –C₄H₉–t | –CH₃ | Oil; IR: 1700 cm⁻¹ |

TABLE 1-continued $$\underset{R^2}{\text{Ar}-N} \begin{array}{c} O \\ \parallel \\ N-R^1 \\ \parallel \\ O \end{array} \quad (I)$$

| Example No. | Ar | R¹ | R² | Physical constants |
|---|---|---|---|---|
| 51 | 2,3,5-trichloro-4-(SCF₃)phenyl | —C₄H₉—t | —C₂H₅ | Oil; IR: 1700 cm⁻¹ |
| 52 | 2,3,5-trichloro-4-(SCF₃)phenyl | —CH₂—C(CH₃)₃ | —CH₃ | Oil; IR: 1700 cm⁻¹ |
| 53 | 2,3,5-trichloro-4-(SCF₃)phenyl | —CH₂—C(CH₃)₃ | —C₂H₅ | Oil, IR: 1705 cm⁻¹ (contains chloroform CHCl₃) |
| 54 | 4-CF₃-phenyl | —C₄H₉—t | —C₂H₅ | mp.: 90° C. |
| 55 | 4-CF₃-phenyl | —CH₂—C(CH₃)₃ | —CH₃ | mp.: 112° C. |
| 56 | 4-CF₃-phenyl | —CH₂—C(CH₃)₃ | —C₂H₅ | mp.: 80° C. |
| 57 | 3-CF₃-phenyl | —CH₂—C(CH₃)₃ | —CH₃ | mp.: 83° C. |
| 58 | 3-CF₃-phenyl | —CH₂—C(CH₃)₃ | —C₂H₅ | mp.: 92° C. |
| 59 | 3-CF₃-phenyl | —C₄H₉—t | —CH₃ | mp.: 82° C. |

TABLE 1-continued (I)

$$\underset{R^2}{Ar-N} \overset{O}{\underset{O}{\bigvee}} \overset{O}{\underset{O}{\bigvee}} R^1$$

| Example No. | Ar | R¹ | R² | Physical constants |
|---|---|---|---|---|
| 60 | 3-CF₃-C₆H₄- | —C₄H₉—n | —CH₃ | mp.: 74° C. |
| 61 | 3-CF₃-C₆H₄- | —CH₂—C₆H₅ | —CH₃ | mp.: 125° C. |
| 62 | 3-CF₃-C₆H₄- | cyclohexyl | —CH₃ | Oil; IR: 1690 cm⁻¹ |
| 63 | 3-CF₃-C₆H₄- | —CH₂-(2-furyl) | —CH₃ | mp.: 146° C. |
| 64 | 3-CF₃-C₆H₄- | —CH₃ | —CH₃ | mp.: 140° C. |
| 65 | 3-CF₃-C₆H₄- | —C₁₂H₂₅ | —CH₃ | mp.: 65° C. |
| 66 | 3-CF₃-C₆H₄- | —C₃H₇—iso | —CH₃ | mp.: 98° C. |
| 67 | 3-Cl-4-CF₃-C₆H₃- | —CH₂—C(CH₃)₃ | —CH₃ | mp.: 123° C. |
| 68 | 3-Cl-4-CF₃-C₆H₃- | —C₄H₉—t | —CH₃ | mp.: 103° C. |

TABLE 1-continued $$\text{Structure (I): Ar-N, R}^1\text{-N, R}^2\text{-N triazine-2,4,6-trione}$$

| Example No. | Ar | R¹ | R² | Physical constants |
|---|---|---|---|---|
| 69 | 3-Cl, 4-CF₃-phenyl | —C₄H₉—t | —iC₃H₇ | $n_D^{20}$: 1.485 |
| 70 | 3-Cl, 4-CF₃-phenyl | —C₄H₉—t | —CH₂—CH=CH₂ | mp.: 80° C. |
| 71 | 3-Cl, 4-CF₃-phenyl | —C₄H₉—t | —CH₂—CN | mp.: 107° C. |
| 72 | 3-Cl, 4-CF₃-phenyl | —C₄H₉—t | —CH₂—COO—C₂H₅ | $n_D^{20}$: 1.485 |
| 73 | 3-Cl, 4-CF₃-phenyl | —C₄H₉—t | —C₂H₅ | $n_D^{20}$: 1.490 |
| 74 | 3-Cl, 4-CF₃-phenyl | —C₄H₉—t | —C₂H₅ | mp.: 130° C. |
| 75 | 3-Cl, 4-CF₃-phenyl | —CH₂—C(CH₃)₃ | —C₂H₅ | mp.: 108° C. |
| 76 | 2-CF₃-phenyl | —C₁₂H₂₅ | —CH₃ | mp.: 64° C. |
| 77 | 4-CF₂CF₂H-phenyl | —CH₂—C(CH₃)₃ | —C₂H₅ | mp.: 136° C. |
| 78 | 4-CF₂CF₂H-phenyl | —C₄H₉—t | —C₂H₅ | mp.: 104° C. |

TABLE 1-continued $$\underset{Ar}{\overset{}{\underset{}{N}}}\underset{}{\overset{O}{\underset{}{\overset{}{\parallel}}}}\underset{}{\overset{}{\underset{R^2}{N}}}\underset{}{\overset{O}{\underset{}{\overset{}{\parallel}}}}R^1 \quad (I)$$

| Example No. | Ar | R¹ | R² | Physical constants |
|---|---|---|---|---|
| 79 | 3-SO₂F-phenyl | —CH₂—C(CH₃)₃ | —CH₃ | mp.: 146° C. |
| 80 | 3-SO₂F-phenyl | —CH₂—C(CH₃)₃ | —C₂H₅ | mp.: 114° C. |
| 81 | 3-SO₂F-phenyl | —CH₂—C(CH₃)₃ | —C₃H₇—iso | mp.: 128° C. |
| 82 | 4-Cl-phenyl | —CH(CH₃)—C₂H₅ | —CH₃ | mp.: 126° C. |
| 83 | 3,4-diCl-phenyl | —C₃H₇—n | —CH₃ | mp.: 94° C. |
| 84 | 3,4-diCl-phenyl | —C₄H₉—t | —CH₃ | mp.: 122° C. |
| 85 | 3,5-diCl-phenyl | —C₃H₇—iso | —CH₃ | Oil; IR: 1695 cm⁻¹ |
| 86 | 3,5-diCl-phenyl | —CH₃ | —CH₂—CH=CH₂ | mp.: 166° C. |
| 87 | 3,5-diCl-phenyl | —C₄H₉—t | —CH₃ | 150–160° C. (decomposition) |

TABLE 1-continued

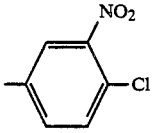

| Example No. | Ar | R¹ | R² | Physical constants |
|---|---|---|---|---|
| 88 | 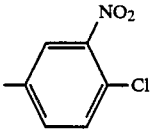 (NO₂, Cl substituted phenyl) | —C₄H₉—t | —CH₃ | mp.: 130° C. |
| 89 | 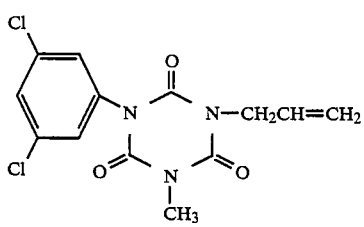 (NO₂, Cl substituted phenyl) | —C₃H₇—iso | —CH₃ | mp.: 185° C. |

TABLE 2

| Example No. | Ar | R¹ | Alkyl | Physical constants |
|---|---|---|---|---|
| 91 | 3,5 Cl₂—C₆H₃ | tert-C₄H₉ | CH₃ | mp.: 160° C. |

Example 90
(Process b)

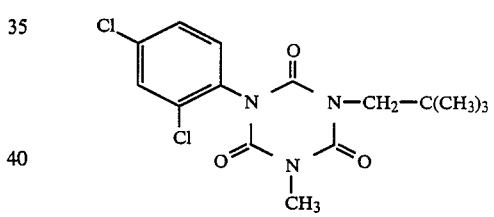

12.3 g (0.05 mol) of N(3,5-dichlorophenyl)-N'-allylurea (melting point 133°–134° C.) are dissolved in 100 ml of dioxane, and 8 g (0.051 mol) of bis-chlorocarbonyl-N-methylamine are added. On warming, HCl escapes continuously. The mixture is heated under reflux for 1 hour, until the evolution of gas has ended. 150 ml of water are added to this reaction solution at room temperature. The reaction product thereby crystallizes. It is filtered off with suction and rinsed with methanol. Yield: 9 g=55% of theory; melting point: 165°–167° C.

The following compounds of the formula

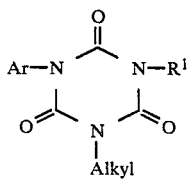

are obtained in an analogous manner:

Example 92
(Process C)

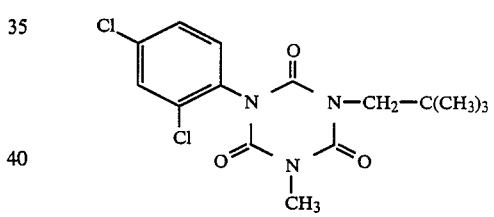

2.5 g (17.4 mmol) of N-methyl-N'-(2,2-dimethylpropyl) urea are dissolved in 20 ml of dioxane, and 5 g (17.4 mmol) of bis-chlorocarbonyl-N-2,4-dichlorophenylamine are added. On warming, HCl escapes continuously. The mixture is heated under reflux for 1 hour, until the evolution of gas has ended. 150 ml of ice-water are added to this solution. The reaction product thereby crystallizes. It is filtered off with suction and recrystallized in a mixture of toluene and petroleum ether.

Yield: 2.2 g=35% of theory;
Melting point=110°–112° C.

The following compounds of the formula

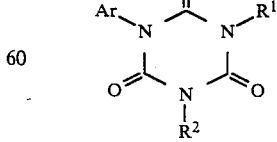

are obtained in an analogous manner.

TABLE 3
| Example No. | Ar | R¹ | R² | Physical Constants |
|---|---|---|---|---|
| 93 | 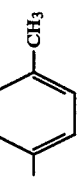 4-CH₃-C₆H₄ | —C(CH₃)₃ | —CH₃ | mp.: 110° C. |
| 94 | 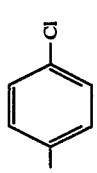 4-Cl-C₆H₄ | —C(CH₃)₃ | —C₃H₇ | $^1H^{CDCL_3}$: 7.48d(2H; J=8Hz); 7.23d(2H; J=8Hz); 3.88dd(2H; J=7+6Hz) 1.74s(9H); 1.73m(2H); 1.00t(3H; J=7Hz) |
| 95 | 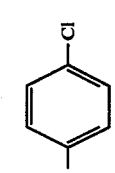 4-Cl-C₆H₄ | —C(CH₃)₃ | —C₂H₅ | mp.: 92° C. |
| 96 | 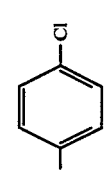 4-Cl-C₆H₄ | —C(CH₃)₃ | —CH₃ | $^1H^{CDCl_3}$:7.46d(2H; J=8Hz); 7.17d (2H; J=8Hz);3.34s(3H); 1.72s(9H) |
| 97 | 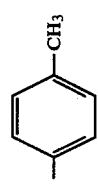 4-CH₃-C₆H₄ | —C(CH₃)₃ | —C₂H₅ | mp.: 114° C. |
| 98 | 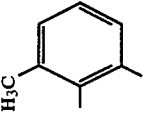 2,6-(CH₃)₂-C₆H₃ | —C(CH₃)₃ | —CH₃ | mp.: 152° C. |
| 99 | 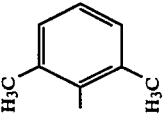 2,6-(CH₃)₂-C₆H₃ | —C(CH₃)₃ | —C₂H₅ | mp.: 110° C. |

TABLE 3-continued

| Example No. | Ar | R¹ | R² | Physical Constants |
|---|---|---|---|---|
| 100 | 2,6-dichlorophenyl | 2,6-dichlorophenyl | —C₂H₅ | mp.: 236° C. |
| 101 | 2,6-dichlorophenyl | 2,6-dichlorophenyl | —CH₃ | mp.: 290° C. |
| 102 | 2,6-dichlorophenyl | —C(CH₃)₃ | —C₂H₅ | mp.: 130° C. |
| 103 | 2,6-dichlorophenyl | —C(CH₃)₃ | —CH₃ | mp.: 130° C. |
| 104 | 2,5-dichlorophenyl | —CH₂—C(CH₃)₃ | —CH₃ | mp.: 111° C. |
| 105 | 4-(trifluoromethoxy)phenyl | —C(CH₃)₂—CH₂—OCH₃ | —C₂H₅ | mp.: 86° C. |

TABLE 3-continued

| Example No. | Ar | R¹ | R² | Physical Constants |
|---|---|---|---|---|
| 106 | 4-methyl-2-chloro-1-(OCF₃)-phenyl | —C(CH₃)₃ | —C₂H₅ | ¹H*DMSO*: 7.85d(1H; J=2Hz); 7.75dbr(1H; J=8Hz); 7.53dd(H; J=2+8Hz); 3.79q(2H; J=7Hz); 1.65s(9H); 1.16t(3H; J=7Hz) |
| 107 | 2-(OCF₃)-phenyl (F₃C—O—) | —C(CH₃)₃ | —C₂H₅ | ¹H*CDCl₃*: 7.42m(4H); 3.97q(2H; J=7Hz); 1.74s(9H); 1.28t(3H; J=7Hz) |
| 108 | 4-methyl-3-chloro-1-(OCF₃)-phenyl | —C(CH₃)₃ | —C₂H₅ | ¹H*DMSO*: 7.83sbr(1H); 7.77d(1H; J=8Hz); 7.57dbr(1H; J=8Hz); 3.82q(2H; J=7Hz); 1.64s(9H); 1.16t(3H; J=7Hz) |
| 109 | 3-methyl-1-(OCF₃)-phenyl | —C(CH₃)₃ | —C₂H₅ | mp.: 61° C. |
| 110 | 4-methyl-1-(OCF₂H)-phenyl | —C(CH₃)₃ | —C₂H₅ | mp.: 102° C. |
| 111 | 4-methyl-1-(OCFCl₂)-phenyl | —C(CH₃)₃ | —C₂H₅ | IR: 1695 cm⁻¹ |
| 112 | 4-methyl-1-(OCF₂—CHClF)-phenyl | —C(CH₃)₃ | —C₂H₅ | IR: 1698 cm⁻¹ |

TABLE 3-continued

| Example No. | Ar | R¹ | R² | Physical Constants |
|---|---|---|---|---|
| 113 | 4-CH₃O-C₆H₄- | -C(CH₃)₃ | -C₂H₅ | IR: 1690 cm⁻¹ |
| 114 | 4-CF₃O-C₆H₄- | -C₂H₅ | -C₂H₅ | mp.: 116° C. |
| 115 | 4-CF₃O-C₆H₄- | -C(CH₃)₂-C₂H₅ | -C₂H₅ | ¹H$DMSO$: 7.47, (4H); 3.78q(2H; J=7Hz); 2.03q(2H; J=7Hz); 1.58s (6H); 1.15t(3H; J=7Hz); 0.85t(3H; J=7Hz) |
| 116 | 4-CF₃O-C₆H₄- | -C(CH₃)₂-CH₂-C(CH₃)₃ | -C₂H₅ | IR: 1692 cm⁻¹ |
| 117 | 4-CF₃O-C₆H₄- | -CH₂-CH₂-C(CH₃)₃ | -C₂H₅ | mp.: 108° C. |
| 118 | 4-(CF₃-CHF-CF₂-O)-C₆H₄- | -C(CH₃)₃ | -C₂H₅ | IR: 1695 cm⁻¹ |
| 119 | 3-(CF₃-CHF-CF₂-O)-C₆H₄- | -C(CH₃)₃ | -C₂H₅ | mp.: 108° C. |
| 120 | 3-(ClFHC-CF₂-O)-C₆H₄- | -C(CH₃)₃ | -C₂H₅ | mp.: 94° C. |

TABLE 3-continued

| Example No. | Ar | $R^1$ | $R^2$ | Physical Constants |
|---|---|---|---|---|
| 121 | 2-Cl, 4-(O-CF$_2$-CHClF)-phenyl | -C(CH$_3$)$_3$ | -C$_2$H$_5$ | mp.: 112° C. |
| 122 | 2-CF$_3$, 4-CH$_3$, 5-CF$_3$-phenyl (F$_3$C-, CF$_3$ substituted methylphenyl) | -C(CH$_3$)$_3$ | -C$_2$H$_5$ | mp.: 96° C. |
| 123 | 3-CH$_3$, 4-CH$_3$, with O-CF$_3$-phenyl | -C(CH$_3$)$_3$ | -C$_2$H$_5$ | mp.: 92° C. |
| 124 | 2-CF$_3$, 4-CH$_3$-phenyl O-CF$_3$ | -C(CH$_3$)$_3$ | -C$_2$H$_5$ | IR: 1685 cm$^{-1}$ |
| 125 | 3-Cl, 4-CH$_3$, with O-CF$_2$-CHClF-phenyl | -C(CH$_3$)$_3$ | -C$_2$H$_5$ | $^1$H$DMSO$: 7.69d(1H; J=8Hz); 7.60d(1H; J=2Hz); 7.45dd(1H; J=2+8Hz); 7.37dt(1H; J=46+4,5Hz); 3.80qbr(2H; J=7Hz); 1.63s(9H); 1.17t(3H; J=7Hz) |
| 126 | 3-Cl, 4-CH$_3$, 5-CF$_3$-phenyl | -C(CH$_3$)$_3$ | -C$_2$H$_5$ | $^1$H$CDCl_3$: 7.82d(1H; J=2Hz); 7.66dd(1H; J=8+2Hz); 7.47d (1H; J=8Hz); 3.97q(2H; J=7Hz); 1.70s(9H); 1.28t(3H; J=7Hz) |
| 127 | 2-NO$_2$-methylphenyl | -C(CH$_3$)$_3$ | -C$_2$H$_5$ | mp.: 154° C. |

TABLE 3-continued

| Example No. | Ar | R¹ | R² | Physical Constants |
|---|---|---|---|---|
| 128 | 4-(CF₃O)-C₆H₄- | —C₄H₉ | —C₂H₅ | mp.: 92° C. |
| 129 | 4-(CF₃O)-C₆H₄- | —CH(CH₃)—C₂H₅ | —C₂H₅ | $^1H\ CDCl_3$: 7.33m(4H); 4.82sextett(1H; J=7Hz); 4.00q(2H; J=7Hz); 2.07quintett d(1H; J=7+17Hz); 1.84quintett d(1H; J=7+17Hz); 1.48d(3H; J=7Hz); 1.29t(3H; J=7Hz); 0.91t(3H; J=7Hz) |
| 130 | 4-(CF₃O)-C₆H₄- | —CH₂—CF₃ | —C₂H₅ | mp.: 116° C. |
| 131 | 4-(CF₃O)-C₆H₄- | —CH₂—CF₃ | —CH(CH₃)₂ | IR: 1695 cm⁻¹ |
| 132 | 4-(CF₃O)-C₆H₄- | 1-methylcyclopentyl | —CH₃ | mp.: 98° C. |
| 133 | 4-(CF₃O)-C₆H₄- | 1-methylcyclopentyl | —C₂H₅ | mp.: 78° C. |
| 134 | 4-(CF₃O)-C₆H₄- | —C(CH₃)₃ | —CH₂—CH=CH₂ | mp.: 68° C. |
| 135 | 4-(CF₃O)-C₆H₄- | —C(CH₃)₃ | —CH₂—C≡CH | mp.: 110° C. |

TABLE 3-continued

| Example No. | Ar | R¹ | R² | Physical Constants |
|---|---|---|---|---|
| 136 | 4-NO₂-C₆H₄ | —C(CH₃)₃ | —C₂H₅ | mp.: 150° C. |
| 137 | 3-OCH₃-C₆H₄ | —C(CH₃)₃ | —C₂H₅ | mp.: 94° C. |
| 138 | 2-OCH₃-C₆H₄ | —C(CH₃)₃ | —C₂H₅ | mp.: 100° C. |
| 139 | 3-OC₂H₅-C₆H₄ | —C(CH₃)₃ | —C₂H₅ | IR: 1680 cm⁻¹ |
| 140 | 2-OC₂H₅-C₆H₄ | —C(CH₃)₃ | —C₂H₅ | mp.: 64° C. |
| 141 | 3-NO₂-C₆H₄ | —C(CH₃)₃ | —C₂H₅ | mp.: 114° C. |
| 142 | 4-Br-C₆H₄ | —C(CH₃)₃ | —C₂H₅ | mp.: 104° C. |

TABLE 3-continued

| Example No. | Ar | R¹ | R² | Physical Constants |
|---|---|---|---|---|
| 143 | 4-C(CH₃)₃-C₆H₄ | —C(CH₃)₃ | —C₂H₅ | IR: 1692 cm⁻¹ |
| 144 | 3,5-Cl₂-4-OCF₃-C₆H₂ | —C(CH₃)₃ | —C₂H₅ | IR: 1690 cm⁻¹ |
| 145 | 4-OCF₃-C₆H₄ | cyclopropyl | —CH₃ | mp.: 116° C. |
| 146 | 4-OCF₃-C₆H₄ | cyclopropyl | —C₂H₅ | mp.: 106° C. |
| 147 | 4-OCF₃-C₆H₄ | cyclopropyl | —CH(CH₃)₂ | IR: 1695 cm⁻¹ |
| 148 | 4-CF₃-C₆H₄ | —C(CH₃)₃ | —CH₃ | mp.: 112° C. |
| 149 | 4-CF₃-C₆H₄ | —C(CH₃)₃ | —CH₂—CH=CH₂ | mp.: 114° C. |
| 150 | 4-CF₃-C₆H₄ | —C(CH₃)₃ | —C₃H₇ | IR: 1690 cm⁻¹ |

TABLE 3-continued

| Example No. | Ar | $R^1$ | $R^2$ | Physical Constants |
|---|---|---|---|---|
| 151 | 4-CF$_3$-C$_6$H$_4$ | —CH(CH$_3$)$_2$ | —C$_2$H$_5$ | mp.: 104° C. |
| 152 | 4-CF$_3$-C$_6$H$_4$ | —CH(CH$_3$)$_2$ | —CH(CH$_3$)$_2$ | mp.: 120° C. |
| 153 | 4-CF$_3$-C$_6$H$_4$ | —CH(CH$_3$)$_2$ | —C$_3$H$_7$ | mp.: 112° C. |
| 154 | 4-CF$_3$-C$_6$H$_4$ | —CH(CH$_3$)$_2$ | —CH$_2$—CH=CH$_2$ | mp.: 124° C. |
| 155 | 4-CF$_2$Cl-O-C$_6$H$_4$ | —CH(CH$_3$)$_3$ | —CH$_3$ | mp.: 89° C. |
| 156 | 4-CF$_2$Cl-O-C$_6$H$_4$ | —CH(CH$_3$)$_3$ | —CH$_2$—CH=CH$_2$ | mp.: 70° C. |
| 157 | 4-CF$_2$Cl-O-C$_6$H$_4$ | —CH(CH$_3$)$_3$ | —C$_3$H$_7$ | mp.: 66° C. |
| 158 | 4-CH$_3$-O-C$_6$H$_4$ | —CH(CH$_3$)$_3$ | —CH$_3$ | mp.: 118° C. |

TABLE 3-continued
| Example No. | Ar | $R^1$ | $R^2$ | Physical Constants |
|---|---|---|---|---|
| 159 | 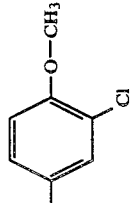 | —C(CH₃)₃ | —CH₃ | mp.: 142° C. |
| 160 | 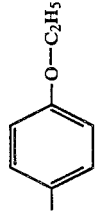 | —C(CH₃)₃ | —CH₂—CH=CH₂ | mp.: 78° C. |
| 161 | 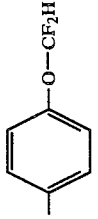 | —C(CH₃)₃ | —CH₂—CH=CH₂ | mp.: 82° C. |
| 162 |  | —C(CH₃)₃ | —CH₃ | IR: 1680 cm⁻¹ |
| 163 |  | —C(CH₃)₃ | —C₃H₇ | mp.: 70° C. |
| 164 | 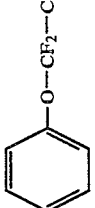 | —C(CH₃)₃ | —CH₂—CH=CH₂ | mp.: 90° C. |
| 165 | 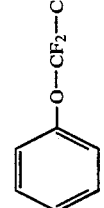 | —C(CH₃)₃ | —CH₃ | mp.: 126° C. |
| 166 | 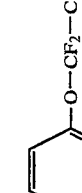 | —C(CH₃)₃ | —C₃H₇ | mp.: 84° C. |

TABLE 3-continued

| Example No. | Ar | R¹ | R² | Physical Constants |
|---|---|---|---|---|
| 167 | 4-(ClFHC-CF$_2$-O)-C$_6$H$_4$- | -C(CH$_3$)$_3$ | -CH$_2$-CH=CH$_2$ | mp.: 92° C. |
| 168 | 4-(CF$_3$-O)-C$_6$H$_4$- | cyclopropyl | -CH$_2$-CH=CH$_2$ | mp.: 106° C. |
| 169 | 4-(CF$_3$-O)-C$_6$H$_4$- | -C$_2$H$_5$ | -CH$_3$ | mp.: 122° C. |
| 170 | 4-(CF$_3$-O)-C$_6$H$_4$- | -C$_2$H$_5$ | -CH$_2$-CH=CH$_2$ | mp.: 78° C. |
| 171 | 4-(F$_2$HC-CF$_2$-O)-C$_6$H$_4$- | -C$_4$H$_9$-t | -C$_2$H$_5$ | mp.: 92° C. |
| 172 | 4-(CF$_3$)-C$_6$H$_4$- | -CH(CH$_3$)$_2$ | -CH$_3$ | mp.: 142° C. |
| 173 | 4-(C(CH$_3$)$_3$)-C$_6$H$_4$- | -CH(CH$_3$)$_2$ | -C$_2$H$_5$ | mp.: 98° C. |
| 174 | 4-(C(CH$_3$)$_3$)-C$_6$H$_4$- | -CH(CH$_3$)$_2$ | -C$_3$H$_7$-n | IR: 2920(m), 1680(s), 1420(vs), 1365(m) cm$^{-1}$ |

TABLE 3-continued

| Example No. | Ar | $R^1$ | $R^2$ | Physical Constants |
|---|---|---|---|---|
| 175 | 4-C(CH$_3$)$_3$-C$_6$H$_4$- | —CH(CH$_3$)$_2$ | —CH$_2$—CH=CH$_2$ | Oil |
| 176 | 4-C(CH$_3$)$_3$-C$_6$H$_4$- | —CH(CH$_3$)$_2$ | —CH$_2$—C≡CH | mp.: 72° C. |
| 177 | 4-C(CH$_3$)$_3$-C$_6$H$_4$- | —C(CH$_3$)$_3$ | —CH$_3$ | mp.: 116° C. |
| 178 | 4-C(CH$_3$)$_3$-C$_6$H$_4$- | —C(CH$_3$)$_3$ | —CH$_2$—CH=CH$_2$ | $^1$H—NMR(CDCl$_3$): 7,50d(2H; J=8Hz), 7,16d(2H; J=8HZ), 5,82ddt(1H; J=10+16+6Hz), 5,33dq (1H; J=16+1Hz), 5,25dq(1H; J=10+1Hz), 4,48dt (2H; J=6+1Hz), 1,70s(9H), 1,32s(9H) |
| 179 | 4-C(CH$_3$)$_3$-C$_6$H$_4$- | —C(CH$_3$)$_3$ | —CH$_2$—C≡CH | mp.: 100° C. |
| 180 | 4-C(CH$_3$)$_3$-C$_6$H$_4$- | —C(CH$_3$)$_3$ | —CH$_2$—C(=CH$_2$)—CH$_3$ | mp.: 120° C. |
| 181 | 4-C(CH$_3$)$_3$-C$_6$H$_4$- | —C(CH$_3$)$_3$ | Z,E —CH$_2$—CH=CH—CH$_3$ | IR: 1695 cm$^{-1}$(vs), 1435(s), 1400(s) |
| 182 | 4-C(CH$_3$)$_3$-C$_6$H$_4$- | —CH$_2$—C(CH$_3$)$_3$ | —CH$_3$ | mp.: 162° C. |

TABLE 3-continued

| Example No. | Ar | R¹ | R² | Physical Constants |
|---|---|---|---|---|
| 183 | 4-CH₃O-C₆H₄ | —C(CH₃)₃ | —C₃H₇—n | ¹H—NMR(DMSO): 7,21d(2H, J=8Hz), 6,97d (2H, J=8Hz), 3,77s 3,70dd(2H; J=6+7Hz), 1,61s(9H), 1,69–1,50m(2H), 0,87t(3J=7Hz). |
| 184 | 4-CH₃O-C₆H₄ | —C(CH₃)₃ | —CH₂—CH=CH₂ | ¹H—NMR(DMSO), 7,23d(2H; J=8Hz), 6,97d(2H; J=8Hz), 5,86d(1H; J=16+10+5)Hz), 5,22dq(1H; J=16+1Hz), 5,15dq(1H; J=10+1 5,35dt(2H; J=5+1Hz), 3,77s(3H), 1,61s(9H). |
| 185 | 4-CH₃O-C₆H₄ | —C(CH₃)₂—C₂H₅ | —C₂H₅ | IR: 1698(vs), 1442(m-s), 1425(m-s), 1405(s), 755 cm⁻¹ |
| 186 | 4-CH₃O-C₆H₄ | —C(CH₃)₂—C₂H₅ | —C₃H₇—n | mp.: 66° C. |
| 187 | 4-CH₃O-C₆H₄ | —C(CH₃)₂—C₂H₅ | —CH₂—CH=CH₂ | IR: 1695(s), 1435(s), 1396(m-s), 755 cm⁻¹(m) |
| 188 | 4-C(CH₃)₃-C₆H₄ | 1-methylcyclopentyl | —C₂H₅ | |
| 189 | 4-CH₃O-C₆H₄ | 1-methylcyclopentyl | —C₃H₇—n | IR: 1698(s), 1680(vs), 1438(vs), 1405 cm⁻¹(s) |
| 190 | 4-CH₃O-C₆H₄ | 1-methylcyclopentyl | —CH₂—CH=CH₂ | |

TABLE 3-continued

| Example No. | Ar | R¹ | R² | Physical Constants |
|---|---|---|---|---|
| 191 | 4-(OCHF₂)C₆H₄ | —C(CH₃)₃ | —C₃H₇—n | ¹H—NMR(CDCl₃)=7,22m(4H), 6,53t(1H; J=73Hz), 3,84dd (2H; J=6+7Hz), 1,70 sext.(2H; J=7Hz), 1,70s(9H), 0,95t(3H; J=7Hz). |
| 192 | 4-(OCHF₂)C₆H₄ | —CH₂—C(CH₃)₃ | —C₂H₅ | mp.: 110° C. |
| 193 | 4-(OCClF₂)C₆H₄ | —CH₂—C(CH₃)₃ | —CH₂—CH=CH₂ | m.: 122° C. |
| 194 | 4-(OCF₃)C₆H₄ | —CH₂—CH₂—Br | —C(CH₃)₃ | ¹H—NMR(CDC₂₃); 7,31m(4H), 4,31t(2H; J=7Hz), 3,61t(2H J=7Hz), 1,71s(3H). |
| 195 | 4-(OCF₃)C₆H₄ | —CH(CH₃)₂ | —C₃H₇—n | mp: 60° |
| 196 | 4-(OCF₃)C₆H₄ | —C(CH₃)₃ | —CH₂—CH₂—CN | ¹H—NMR(CDCl₃); 7,37m(4H), 4,22t(2H; J=6,5Hz), 2,80 (2H; J=6,5Hz), 1,72s(9H) |
| 197 | 4-(OCF₃)C₆H₄ | —C(CH₃)₃ | —C₄H₉—n | IR: 1695 cm⁻¹ |
| 198 | 4-(OCF₃)C₆H₄ | —C(CH₃)₂—CF₃ | —C₂H₅ | mp.: 118° C. |

TABLE 3-continued
| Example No. | Ar | $R^1$ | $R^2$ | Physical Constants |
|---|---|---|---|---|
| 199 | 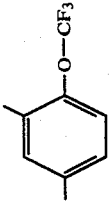 | —C(CH$_3$)$_3$ | —CH$_3$ | mp.: 118° C. |
| 200 | 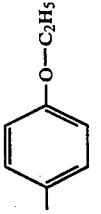 | —C(CH$_3$)$_2$—C$_2$H$_5$ | —C$_2$H$_5$ | IR (CHCl$_3$); 1682 cm$^{-1}$ |
| 201 | 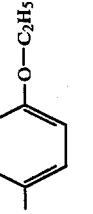 | —C(CH$_3$)$_2$—C$_2$H$_5$ | —C$_3$H$_7$—n | IR: 1688 cm$^{-1}$ |
| 202 | 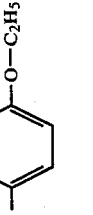 | —C(CH$_3$)$_2$—C$_2$H$_5$ | —CH$_2$—CH=CH$_2$ | IR: 1688 cm$^{-1}$ |
| 203 | 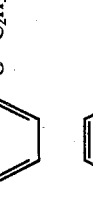 |  | —C$_2$H$_5$ | |
| 204 | 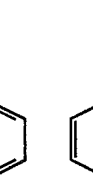 |  | —C$_3$H$_7$—n | |
| 205 |  |  | —CH$_2$—CH=CH$_2$ | IR: 1410 cm$^{-1}$(vs) |
| 206 |  | C(CH$_3$)$_3$ | —C$_4$H$_9$—n | mp.: 76° C. |

TABLE 3-continued

| Example No. | Ar | R¹ | R² | Physical Constants |
|---|---|---|---|---|
| 207 | 4-($HCF_2-CF_2-O$)-phenyl | $-CH_2-C(CH_3)_3$ | $-CH_3$ | mp.: 114° C. |
| 208 | 4-($ClFHC-CF_2-O$)-phenyl | $-C(CH_3)_3$ | $-CH_2-C\equiv CH$ | mp.: 120° C. |
| 209 | 4-($ClFHC-CF_2-O$)-phenyl | $-C(CH_3)_3$ | Z,E $-CH_2-CH=CH-CH_3$ | Gemisch; IR: 1680–1710(s), 1435 cm⁻¹(vs) |
| 210 | 4-($ClFHC-CF_2-O$)-phenyl | $-C(CH_3)_3$ | $-CH_2-C(=CH_2)-CH_3$ | mp.: 114° C. |
| 211 | 4-($C_3H_7-O$)-phenyl | $-C(CH_3)_3$ | $-C_2H_5$ | IR: 2920(m-s), 1698(vs), 1440(m-s), 1422(m-s), 1400(s), 755 cm⁻¹(s) |
| 212 | 4-($(CH_3)_2CH-O$)-phenyl | $-C(CH_3)_3$ | $-C_2H_5$ | IR(CHCl₃): 1695 cm⁻¹(vs) |
| 213 | 2-Cl-4-($(CH_3)_3C-O$)-phenyl | $-C(CH_3)_3$ | $-C_2H_5$ | ¹H-NMR(CDCl₃): 7,32d(1H; J=2Hz), 7,21d(1H; J=8Hz), 7,080d(1H; J=8+2Hz), 3,97q(2H, J=7Hz), 1,73s(9H), 1,48s(9H), 1,29t(3H; J=7Hz). |
| 214 | 3-$CF_3$-4-($HCF_2-CF_2-O$)-phenyl | $-C(CH_3)_3$ | $-C_2H_5$ | ¹H-NMR(DMSO): 7,76d(1H; J=8Hz), 7,67d(1H; J=2Hz), 7,370(1H; J=8+2Hz); 3,79q(2H; J=7Hz), 1,61s(9H), 1,31s(9H), 1,16t(3H; J=7Hz). |

TABLE 3-continued

| Example No. | Ar | R¹ | R² | Physical Constants |
|---|---|---|---|---|
| 215 | 4-N(CH₃)₂-C₆H₄ | —C(CH₃)₃ | C₃H₇—n | mp.: 88° C. |
| 216 | 4-N(CH₃)₂-C₆H₄ | —C(CH₃)₃ | —CH₂—CH=CH₂ | $^1$H—NMR(CDCl₃): 7,07d(2H; J=8Hz), 6,73d(2H; J=8Hz), 5,91t(1H; J=6+10Hz), 5,31dq(1H; J=16+1Hz), 5,23dq(1H; J=10+1Hz 4,47dt(2H; J=6+1Hz), 2,96s(6H), 1,69s(9H). |

USE EXAMPLES

Example A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, a clearly superior activity compared with the prior art is shown by the compounds according to Preparation Examples 1, 9, 10, 14, 29, 30, 37, 54, 68, 73 and 78.

Example B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, for example, a clearly superior activity compared with the prior art is shown by the compounds according to Preparation Examples 1, 9, 10, 29, 30, 54, and 78.

It will be appreciated that the instant specification and examples are set forth by way of illustration and not limitation, and that various modifications and changes may be made without departing from the spirit and scope of the present invention.

What is claimed is:

1. A method of combating fungi which comprises applying to such fungi or to a fungus habitat a fungicidally effective amount of a trisubstituted 1,3,5-triazine-2,4,6-trione of the formula

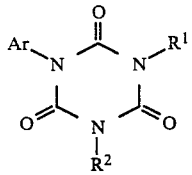

in which

Ar represents phenyl, which is optionally mono-, di-, tri-, tetra- or pentasubstituted by identical or different substituents from the group comprising halogen, alkyl with 1 to 4 carbon atoms, halogenoalkyl with 1 to 4 carbon atoms and 1 to 5 identical or different halogen atoms, alkoxy with 1 to 4 carbon atoms, halogenoalkoxy with 1 to 4 carbon atoms and 1 to 5 identical or different halogen atoms, alkythio with 1 to 4 carbon atoms, and halogenoalkylthio with 1 to 4 carbon atoms and 1 to 5 identical or different halogen atoms, or represents halogenosulphonyl, or represents dialkylamino with identical or different straight-chain or branched alkyl radicals with in each case 1 to 4 carbon atoms and nitro, $R^1$ represents straight-chain or branched alkyl which has 1 to 12 carbon atoms and is optionally mono-or polysubstituted by identical or different substituents from the group comprising halogen, alkoxy with 1 to 3 carbon atoms, halogenoalkoxy with 1 to 2 carbon atoms and 1 to 5 identical or different halogen atoms, alkylthio with 1 to 3 carbon atoms, halogenoalkylthio with 1 or 2 carbon atoms and 1 to 5 identical or different halogen atoms and furyl and phenyl, which can likewise be mono-, di-, tri-, tetra- or pentasubstituted by identical or different halogen atoms; or represents cycloalkyl which has 3 to 8 carbon atoms and is optionally mono-, di-, tri-, tetra-, penta- or hexasubstituted by identical or different substituents from the group comprising halogen, alkyl with 1 to 4 carbon atoms, alkoxy with 1 to 3 carbon atoms, halogenoalkoxy with 1 or 2 carbon atoms and 1 to 5 identical or different halogen atoms, alkylthio with 1 to 3 carbon atoms and halogenoalkylthio with 1 or 2 carbon atoms and 1 to 5 identical or different halogen atoms, and $R^2$ represents alkyl with 1 to 4 carbon atoms, alkenyl with 3 to 5 carbon atoms, alkinyl with 3 to 5 carbon atoms, alkoxyalkyl with in each case 1 to 3 carbon atoms in the alkoxy part and in the alkyl part, alkylthioalkyl with in each case 1 to 3 carbon atoms in the alkylthio part and in the alkyl part or alkoxycarbonylalkyl with 1 to 3 carbon atoms in the alkoxy part and 2 or 3 carbon atoms in the alkyl part, or represents cyanoalkyl with 1 to 5 carbon atoms in the alkyl part, with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals.

2. The method according to claim 1, in which

Ar represents phenyl which is optionally mono-, di-, tri- or tetrasubstituted by identical or different substituents from the group comprising fluorine, chlorine, bromine, alkyl with 1 to 3 carbon atoms, halogenoalkyl with 1 to 3 carbon atoms and 1 to 5 chlorine and/or fluorine atoms, alkoxy with 1 to 3 carbon atoms, halogenoalkoxy with 1 or 2 carbon atoms and 1 to 5 chlorine and/or fluorine atoms, alkylthio with 1 or 2 carbon atoms, halogenoalkylthio with 1 to 3 carbon atoms and 1 to 5 chlorine and/or fluorine atoms, fluorosulphonyl, dialkylamino with identical or different straight-chain or branched alkyl radicals with in each case 1 to 3 carbon atoms and nitro, $R^1$ represents straight-chain or branched alkyl which has 1 to 12 carbon atoms and can be mono-, di-, or trisubstituted by identical or different substituents from the group comprising fluorine, chlorine, alkoxy with 1 or 2 carbon atoms, halogenoalkoxy with 1 or 2 carbon atoms and 1 to 3 chlorine and/or fluorine atoms, alkylthio with 1 or 2 carbon atoms, halogenoalkylthio with 1 or 2 carbon atoms and 1 to 3 chlorine and/or fluorine atoms and furyl and phenyl, which can optionally be mono-, di- or trisubstituted by identical or different substituents from the group comprising chlorine and fluorine, or represents cycloalkyl which has 3 to 6 carbon atoms and is optionally mono-, di-, tri-, tetra-, penta- or hexasubstituted by identical or different substituents from the group comprising fluorine, chlorine, alkyl with 1 or 2 carbon atoms, alkoxy with 1 or 2 carbon atoms, halogenoalkoxy with 1 or 2 carbon atoms and 1 to 5 chlorine and/or fluorine atoms, alkylthio with 1 or 2 carbon atoms and halogenoalkylthio with 1 or 2 carbon atoms and with 1 to 3 chlorine and/or fluorine atoms, and $R^2$ represents alkyl with 1 to 3 carbon atoms, alkenyl with 3 or 4 carbon atoms, alkinyl with 3 or 4 carbon atoms, alkoxyalkyl with 1 or 2 carbon atoms in the alkoxy part and 1 to 3 carbon atoms in the alkyl part, alkylthioalkyl with 1 or 2 carbon atoms in the alkylthio part and 1 to 3 carbon atoms in the alkyl part, alkoxycarbonylalkyl with 1 or 2 carbon atoms in the alkoxy part and 2 or 3 carbon atoms in the alkyl part or cyanoalkyl with 1 to 3 carbon atoms in the alkyl part, with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals.

3. The method according to claim 1, in which

Ar represents phenyl which is optionally mono-, di-, tri- or tetrasubstituted by identical or different substituents from the group comprising fluorine, chlorine, methyl, ethyl, isopropyl, trichloromethyl, trifluoromethyl, tetrachloroethyl, tetrafluoroethyl, methoxy, ethoxy, propoxy, trifluoromethoxy, difluorochloromethoxy, trifluoromethylthio, fluorosulphonyl, chlorosuphonyl, dimethylamino, diethylamino and/or nitro, $R^1$ represents straight-chain or branched alkyl with 1 to 12 carbon atoms, or represents cyclohexyl, furylmethyl or benzyl and $R^2$ represents straight-chain or branched alkyl with 1 to 5 carbon atoms, or represents cyanomethyl, 2-cyanoethyl, methoxycarbonylmethyl, ethoxycarbonylmethyl, n-propoxycarbonylmethyl, allyl or propargyl, with the provisos that (a) when Ar is unsubstituted phenyl $R^1$ and $R^2$ are not alkyl or alkenyl, and (b) when Ar is phenyl substituted by 1 or 2 halogen, lower alkyl, nitro, lower alkoxycarbonyloxy or lower monoalkylcarbonyloxy radicals $R^1$ and $R^2$ are not identical alkyl radicals.

4. The method according to claim 1, wherein such compound is 1-(4-trifluoromethoxyphenyl)-3-t-butyl-5-methyl-1,3,5-triazine-2,4,6-trione of the formula

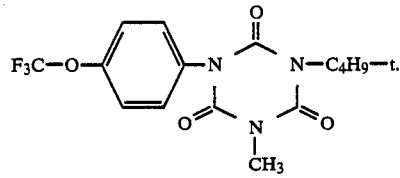

5. The method according to claim 1, wherein such compound is 1-(4-trifluoromethoxyphenyl)-3-t-butyl-5-ethyl-1,3,5-triazine-2,4,6-trione of the formula

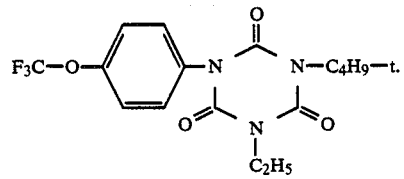

6. The method according to claim 1, wherein such compound is 1-(4-ethoxyphenyl)-3-t-butyl-5-ethyl-1,3,5-triazine-2,4,6-trione of the formula

7. The method according to claim 1, wherein such compound is 1-[4-(1,1,2,2-tetrafluoroethyl)-phenyl]-3-t-butyl-5-ethyl-1,3,5-triazine-2,4,6-trione of the formula

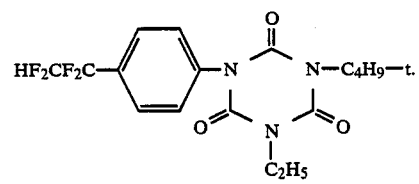

8. The method according to claim 1, wherein such compound is 1-[4-(chlorodifluoromethoxy)-phenyl]-3-t-butyl-5-ethyl-1,3,5-triazine-2,4,6-trione of the formula

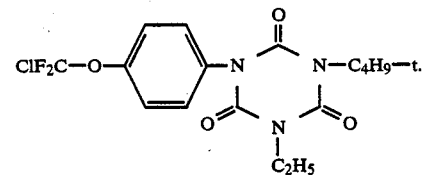

9. A method of combating fungi which comprises applying to such fungi or to a fungus habitat a fungicidally effective amount of a trisubstituted 1,3,5-triazine-2,4,6-trione of the formula

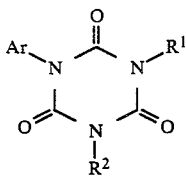

in which
- Ar represents phenyl, which is mono-, di-, tri-, tetra- or pentasubstituted by identical or different substituents from the group comprising halogen, alkyl with 1 to 4 carbon atoms, halogenoalkyl, with 1 to 4 carbon atoms and 1 to 5 identical or different halogen atoms, alkoxy with 1 to 4 carbon atoms, halogenoalkoxy with 1 to 4 carbon atoms and 1 to 5 identical or different halogen atoms, alkylthio with 1 to 4 carbon atoms, halogenoalkylthio with 1 to 4 carbon atoms and 1 to 5 identical or different halogen atoms, halogenosulphonyl, dialkylamino with identical or different straight-chain or branched alkyl radicals with in each case 1 to 4 carbon atoms or nitro,
- $R^1$ represents straight-chain or branched alkyl which has 1 to 12 carbon atoms and is optionally mono-or polysubstituted by identical or different substituents from the group comprising alkoxy with 1 to 3 carbon atoms, halogenoalkoxy with 1 or 2 carbon atoms and 1 to 5 identical or different halogen atoms, alkylthio with 1 to 3 carbon atoms, halogenoalkylthio with 1 or 2 carbon atoms and 1 to 5 identical or different halogen atoms and furyl and phenyl, which can likewise be mono-, di-, tri-, tetra- or pentasubstituted by identical or different halogen atoms; or represents cycloalkyl which has 3 to 8 carbon atoms and is optionally mono-, di-, tri-, tetra-, penta-or hexasubstituted by identical or different substituents from the group comprising halogen, alkyl with 1 to 4 carbon atoms, alkoxy with 1 to 3 carbon atoms, halogenoalkoxy with 1 or 2 carbon atoms and 1 to 5 identical or different halogen atoms, alkylthio with 1 to 3 carbon atoms and halogenoalkylthio with 1 or 2 carbon atoms and 1 to 5 identical or different halogen atoms, and
- $R^2$ is different from $R^1$ and represents alkyl with 1 to 4 carbon atoms, alkenyl with 3 to 5 carbon atoms, alkinyl with 3 to 5 carbon atoms, alkoxyalkyl with in each case 1 to 3 carbon atoms in the alkoxy part and in the alkyl part, alkylthioalkyl with in each case 1 to 3 carbon atoms in the alkylthio part and in the alkyl part or alkoxycarbonylalkyl with 1 to 3 carbon atoms in the alkoxy part and 2 or 3 carbon atoms in the alkyl part, or represents cyanoalkyl with 1 to 5 carbon atoms in the alkyl part.

10. The method according to claim 9, in which
Ar represents phenyl, which is mono-, di-, tri-, or tetrasubstituted by identical or different substituents from the group comprising fluorine, chlorine, bromine, alkyl with 1 to 3 carbon atoms, halogenoalkyl with 1 to 3 carbon atoms and 1 to 5 chlorine and/or fluorine atoms, alkoxy with 1 to 3 carbon atoms, halogenoalkoxy with 1 or 2 carbon atoms and 1 to 5 chlorine and/or fluorine atoms, alkylthio with 1 or 2 carbon atoms, halogenoalkylthio with 1 to 3 carbon atoms and 1 to 5 chlorine and/or fluorine atoms, fluorosulphonyl, dialkylamino with identical or different straight-chain or branched alkyl radicals with in each case 1 to 3 carbon atoms or nitro,
- $R^1$ represents straight-chain or branched alkyl which has 1 to 12 carbon atoms and can be mono-, di-, or trisubstituted by identical or different substituents from the group comprising alkoxy with 1 or 2 carbon atoms, halogenoalkoxy with 1 or 2 carbon atoms and 1 to 3 chlorine and/or fluorine atoms, alkylthio with 1 or 2 carbon atoms, halogenoalkythio with 1 or 2 carbon atoms and 1 to 3 chlorine and/or fluorine atoms and furyl and phenyl, which can optionally be mono-, di- or trisubstituted by identical or different substituents from the group comprising chlorine and fluorine, or represents cycloalkyl which has 3 to 6 carbon atoms and is optionally mono-, di-, tri-, tetra-, penta- or hexasubstituted by identical or different substituents from the group comprising fluorine, chlorine, alkyl with 1 or 2 carbon atoms, alkoxy with 1 or 2 carbon atoms, halogenoalkoxy with 1 or 2 carbon atoms and 1 to 5 chlorine and/or fluorine atoms, alkylthio with 1 or 2 carbon atoms and halogenoalkylthio with 1 or 2 carbon atoms and with 1 to 3 chlorine and/or fluorine atoms, and
- $R^2$ is different from $R^1$ and represents alkyl with 1 to 3 carbon atoms, alkinyl with 3 or 4 carbon atoms, alkenyl with 3 or 4 carbon atoms, alkoxyalkyl with 1 or 2 carbon atoms in the alkoxy part and 1 to 3 carbon atoms in the alkyl part, alkylthioalkyl with 1 or 2 carbon atoms in the alkylthio part and 1 to 3 carbon atoms in the alkyl part, alkoxycarbonylalkyl with 1 or 2 carbon atoms in the alkoxy part and 2 or 3 carbon atoms in the alkyl part or cyanoalkyl with 1 to 3 carbon atoms in the alkyl part.

11. The method according to claim 9, in which
Ar represents phenyl which is mono-, di-, tri- or tetrasubstituted by identical or different substituents from the group comprising fluorine, chlorine, methyl, ethyl, isopropyl, trichloromethyl, trifluoromethyl, tetrachloroethyl, tetrafluoroethyl, methoxy, ethoxy, propoxy, trifluoromethoxy, difluorochloromethoxy, trifluoromethylthio, fluorosulphonyl, chlorosulphonyl, dimethylamino, diethylamino and/or nitro,
- $R^1$ represents straight-chain or branched alkyl with 1 to 12 carbon atoms, or represents cyclohexyl, furylmethyl or benzyl, and
- $R^2$ is different from $R^1$ and represents straight-chain or branched alkyl with 1 to 5 carbon atoms, or represents cyanomethyl, 2-cyanoethyl, methoxycarbonylmethyl, ethoxycarbonylmethyl, n-propoxycarbonylmethyl, allyl or propargyl.

* * * * *